United States Patent
Chkoundali et al.

(10) Patent No.: US 10,332,628 B2
(45) Date of Patent: Jun. 25, 2019

(54) METHOD AND SYSTEM FOR CONTROL OF AN ELECTROMECHANICAL MEDICAL DEVICE

(71) Applicant: SAP SE, Walldorf (DE)

(72) Inventors: Wissem Chkoundali, Walldorf (DE); Nico Rothinger, Walldorf (DE); Markus Mueller, Walldorf (DE); Jonathan Grigo, Walldorf (DE); Sebastian Mietke, Walldorf (DE)

(73) Assignee: SAP SE, Walldorf (DE)

( * ) Notice: Subject to any disclaimer, the term of this patent is extended or adjusted under 35 U.S.C. 154(b) by 295 days.

(21) Appl. No.: 15/281,128

(22) Filed: Sep. 30, 2016

(65) Prior Publication Data

US 2018/0096108 A1    Apr. 5, 2018

(51) Int. Cl.
*G01M 1/38* (2006.01)
*G16H 40/63* (2018.01)
*G05B 19/042* (2006.01)

(52) U.S. Cl.
CPC ......... *G16H 40/63* (2018.01); *G05B 19/0426* (2013.01); *G05B 2219/13023* (2013.01); *G05B 2219/23272* (2013.01); *G05B 2219/2652* (2013.01); *G05B 2219/36231* (2013.01)

(58) Field of Classification Search
CPC ................ G16H 40/63; G05B 19/0426; G05B 2219/2652; G05B 2219/23272; G05B 2219/13023; G05B 2219/36231
See application file for complete search history.

(56) References Cited

U.S. PATENT DOCUMENTS

| | | | | |
|---|---|---|---|---|
| 5,379,036 A | * | 1/1995 | Storer | G06T 9/005 341/51 |
| 5,555,169 A | | 9/1996 | Namba et al. | |
| 5,835,635 A | * | 11/1998 | Nozaki | G06K 9/723 382/226 |
| 5,934,708 A | * | 8/1999 | Batjuk | G09B 19/08 283/117 |
| 6,250,309 B1 | * | 6/2001 | Krichen | A61N 1/37282 128/899 |
| 6,278,975 B1 | | 8/2001 | Brant et al. | |
| 6,847,316 B1 | * | 1/2005 | Keller | H04L 12/66 341/106 |
| 9,715,375 B1 | * | 7/2017 | Lee | G06F 8/427 |

(Continued)

FOREIGN PATENT DOCUMENTS

WO   WO-2015/116151 A1   8/2015

OTHER PUBLICATIONS

Search Report for corresponding European Application No. 16191802.4 dated Apr. 20, 2017.

*Primary Examiner* — Adam Lee
(74) *Attorney, Agent, or Firm* — Harness, Dickey & Pierce, P.L.C.

(57) ABSTRACT

A method comprises receiving by a control system a sequence of symbols, translating the received sequence of symbols into a batch of commands parsable by an electronic controller of the electromechanical medical device, sending the batch of commands from the control system to the electromechanical device, and causing by the electronic controller the electromechanical medical device to execute the batch of commands on the electromechanical medical device.

19 Claims, 6 Drawing Sheets

(56) References Cited

U.S. PATENT DOCUMENTS

| | | | | |
|---|---|---|---|---|
| 2002/0198971 A1* | 12/2002 | Resnick | G06F 9/4448 | 709/221 |
| 2004/0039261 A1* | 2/2004 | Bardy | A61B 5/0006 | 600/300 |
| 2004/0249575 A1* | 12/2004 | Hellmold | A61B 6/00 | 702/19 |
| 2005/0091036 A1* | 4/2005 | Shackleton | G06F 17/2705 | 704/9 |
| 2006/0193519 A1* | 8/2006 | Sternby | G06K 9/00416 | 382/186 |
| 2006/0239560 A1* | 10/2006 | Sternby | G06K 9/00416 | 382/187 |
| 2007/0232866 A1* | 10/2007 | Nephin | G06F 19/3418 | 600/300 |
| 2007/0233521 A1* | 10/2007 | Wehba | A61M 5/142 | 705/3 |
| 2008/0059598 A1* | 3/2008 | Garibaldi | G16H 40/63 | 709/208 |
| 2008/0114618 A1* | 5/2008 | Pysnik | G06Q 10/10 | 705/3 |
| 2008/0183459 A1* | 7/2008 | Simonsen | G06F 17/289 | 704/1 |
| 2008/0275853 A1* | 11/2008 | Vail | H04L 67/36 | |
| 2009/0066641 A1* | 3/2009 | Mahajan | A63F 13/10 | 345/156 |
| 2009/0171512 A1* | 7/2009 | Duncan | F24F 5/0035 | 700/300 |
| 2010/0090694 A1* | 4/2010 | Heid | A61B 5/055 | 324/309 |
| 2011/0033095 A1* | 2/2011 | Hale | G06F 17/2785 | 382/131 |
| 2011/0092907 A1* | 4/2011 | Krogh | G06Q 50/22 | 604/151 |
| 2011/0105854 A1* | 5/2011 | Kiani | G16H 40/63 | 600/300 |
| 2012/0185496 A1* | 7/2012 | Magdy | G06F 17/2818 | 707/760 |
| 2013/0045685 A1* | 2/2013 | Kiani | G06F 19/3406 | 455/41.2 |
| 2013/0185050 A1* | 7/2013 | Bird | G06F 17/30654 | 704/2 |
| 2014/0025703 A1* | 1/2014 | Samuels | G06F 17/30424 | 707/769 |
| 2014/0101545 A1* | 4/2014 | Paek | G06F 3/016 | 715/702 |
| 2014/0135588 A1* | 5/2014 | Al-Ali | G06F 19/00 | 600/300 |
| 2014/0188856 A1* | 7/2014 | Jiang | G06F 17/30669 | 707/723 |
| 2015/0097701 A1* | 4/2015 | Al-Ali | A61B 5/0002 | 340/870.07 |
| 2015/0294580 A1* | 10/2015 | Kullok | G09B 7/02 | 434/362 |
| 2015/0332197 A1* | 11/2015 | Sharma | G16H 40/20 | 705/2 |
| 2016/0225369 A1 | 8/2016 | Agrawal et al. | | |
| 2016/0259780 A1 | 9/2016 | Panemangalore et al. | | |
| 2017/0061079 A1* | 3/2017 | LaValley | G06F 19/325 | |

* cited by examiner

METHOD AND SYSTEM FOR CONTROL OF AN ELECTROMECHANICAL MEDICAL DEVICE

TECHNICAL FIELD

This invention relates to electronic systems for controlling electromechanical medical devices. In particular, this invention relates to a failure free operation of the electromechanical medical devices using sequences of symbols received from user electronic interface devices.

BACKGROUND

A lot of medical electromechanical devices are equipped with electronic controllers for controlling of their operation. Not only complex medical tools like magnetic resonance imaging or various X-Ray systems but simple ones like syringes are equipped with numerous electronic controllers of different types. Computerization of medical tools enables integrating them in computer networks and executing remote operation of them via user electronic device interfaces. Such a user electronic device interface can be provided on a smartphone or any hand held computer device. As a result the user electronic device interface devices have to be equipped with different input-output (I/O) ports supporting various computer network protocols for communication with different medical tools. In addition the user electronic interface devices have to communicate with the medical tools using different commands. This diversity of commands, protocols, data types, etc. can make programming and/or configuring of the user interface electronic devices very difficult. Moreover, the user electronic interface devices have to provide failure free operation of the medical tools, since this aspect is of particular importance in the healthcare sector.

SUMMARY

Symbol, as understood here, can be a word, a combination of words, an icon, a pictogram, a number in any format, a combination of one or more icons and/or one or more pictograms and/or one or more word.

Natural language, as understood here, is any language that has evolved naturally in humans through use and repetition without conscious planning or premeditation. Natural languages can take different forms, such as speech, signing, or writing. They are distinguished from constructed and formal languages such as those used to program computers. An example of a natural language can be an English language or a German language.

Syntax of a natural language, as understood here, is the set of rules, principles, and processes that govern the structure of sentences in a given language, specifically word order.

The disclosure generally describes a control method for controlling of electromechanical medical devices, a computer-readable media storing computer executable instructions for executing the control method, and a control system for controlling the electromechanical medical devices. The aforementioned inventive solutions can be used for operating of a control system operable for translating sequences of symbols received by the control system into batches of commands being executable by electronic controllers providing operation of electromechanical medical devices. The sequences of symbols can be formulated for instance a natural language, e.g. English or German. This functionality can enable operating of the electromechanical medical devices using widely used user interfaces operated on different devices without the need to customize the user interface and/or the device supporting it for operation of a particular electromechanical medical device.

In addition, the control system can send the description of the batch of commands being a translation of a sequence of symbols received from a user electronic interface device back to it for verification. The batch of commands is executed only after receiving a confirmation from the user electronic interface device that the description of the batch of commands corresponds to the sequence of symbols. The confirmation can be generated by prompting a user of the user electronic interface device to confirm that the description of the batch of commands corresponds to the sequence of symbols.

It is an objective of embodiments of the invention to provide for a control system configured to provide effective operation of the electromechanical medical devices, a control method for performing same, and a computer readable medium having stored thereon a computer executable program code for executing the control method.

According to one embodiment, the present invention relates to a control system for controlling an electromechanical medical device. The control system comprises a computer processor and a memory storing instructions of a computer executable code which execution by the computer processor causes the control system to perform the following: receiving by the control system a sequence of symbols; translating the received sequence of symbols into a batch of commands parsable by an electronic controller of the electromechanical medical device; sending the batch of commands from the control system to the electromechanical device; and causing by the electronic controller the electromechanical medical device to execute the batch of commands on the electromechanical medical device.

According to another embodiment, the present invention relates to a control method for controlling an electromechanical medical devices. The method comprises the following: receiving by a control system a sequence of symbols; translating the received sequence of symbols into a batch of commands parsable by an electronic controller of the electromechanical medical device; sending the batch of commands from the control system to the electromechanical device; and causing by the electronic controller the electromechanical medical device to execute the batch of commands on the electromechanical medical device.

According to another embodiment, the present invention relates to a computer readable medium having stored thereon a computer executable code for execution by a computer processor controlling a control system, wherein execution of the instructions of the executable code causes the computer processor to execute the control method of the aforementioned embodiment.

These embodiments can be advantageous because they can enable effective operation of the electromechanical medical devices. The control system can receive sequences of symbols of different types and in different formats and translate them into batches of commands parsable by controllers of electromechanical medical devices. As a result thereof the electromechanical medical devices can be operated using a broad spectrum of electronic devices, e.g. handheld electronic devices comprising electronic user interfaces.

The details of one or more implementations of the subject matter of this specification are set forth in the accompanying drawings and the description below. Other features, aspects, and advantages of the subject matter will become apparent from the description, the drawings, and the claims.

DETAILED DESCRIPTION

Figure 1:
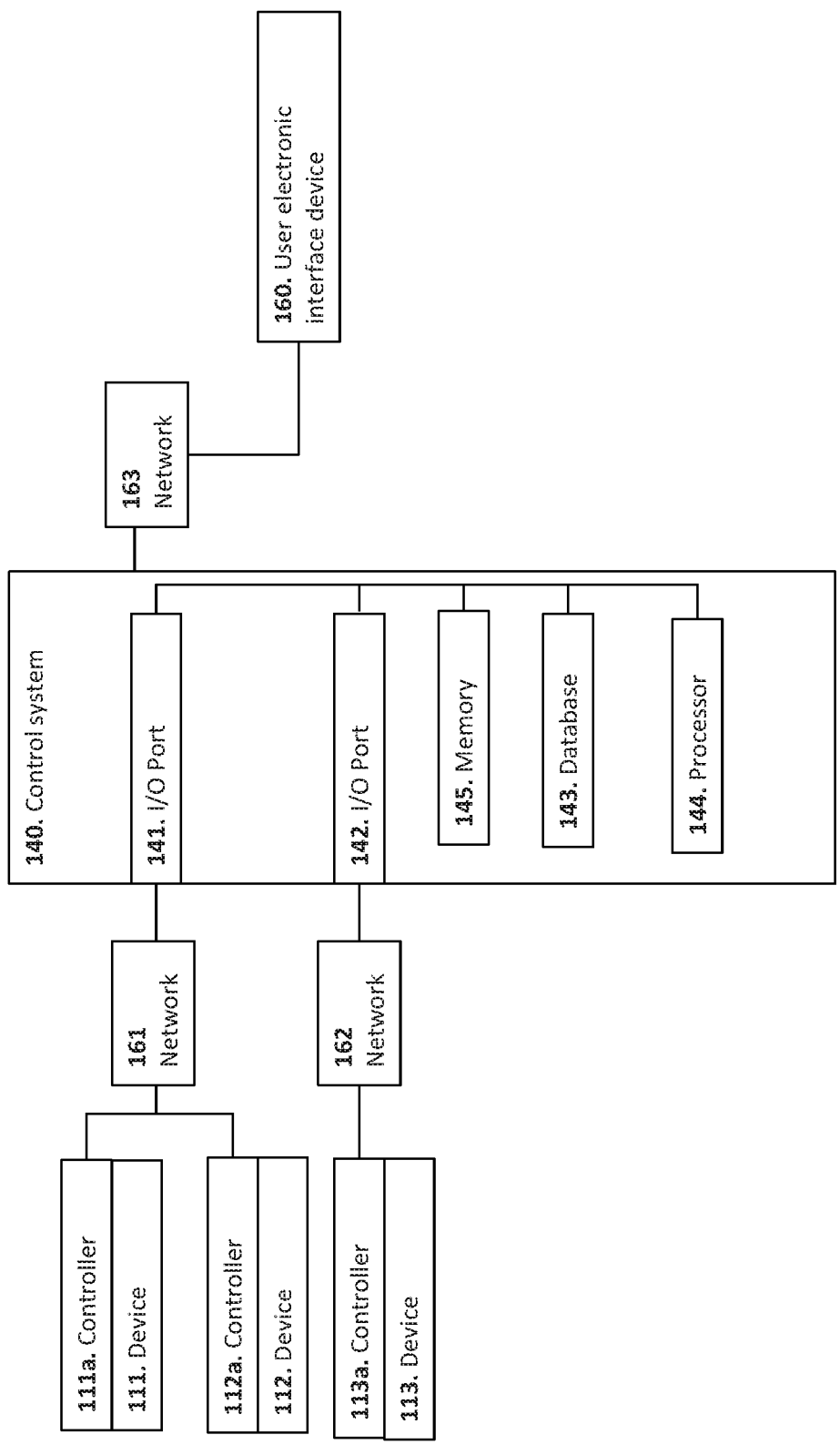
FIG. 1 is a block diagram illustrating an example environment for controlling electromechanical medical devices.

This disclosure generally describes computer-implemented methods, computer-readable media, and control systems for controlling electromechanical medical devices. The electromechanical medical device can be for instance a syringe, a perfusion tool, a magnetic resonance imaging system, an X-Ray tool, a patient monitoring system, etc. The following description is presented to enable any person skilled in the art to practice the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

According to another embodiment, the translating of the received sequence of symbols is executed using dictionaries. Each of the dictionaries has a respective batch of commands parsable by the electronic controller of the electromechanical medical device and respective first sets of symbols corresponding to the respective batch of commands parsable by the electronic controller of the electromechanical medical device. The translating of the received sequence of symbols into the batch of commands parsable by the electronic controller of the electromechanical medical device comprises the following steps: identifying a set of dictionaries, wherein each first set of symbols of any dictionary of the set of dictionaries comprises a respective symbol being comprised in the received sequence of symbols; identifying for each of the dictionaries of the set of dictionaries a respective fragment of the received sequence of symbols comprising one symbol of each of the first sets of symbols of the each of the dictionaries, starting with the symbol comprised in one of the first sets of symbols of the each of the dictionaries, and ending with the symbol comprised in another one of the first sets of symbols of the each of the dictionaries; selecting the identified fragment of the received sequence of symbols having the least number of symbols among the identified fragments of the received sequence of symbols; and selecting the dictionary corresponding to the selected identified fragment of the received sequence of symbols. The batch of commands of the selected dictionary is the one generated in the translating of the received sequence of symbols into the batch of commands parsable by the electronic controller of the electromechanical medical device.

According to another embodiment, the identifying for each of the dictionaries of the set of dictionaries of the respective fragment of the received sequence of symbols comprising one symbol of each of the first sets of symbols of the each of the dictionaries, starting with the symbol comprised in one of the first sets of symbols of the each of the dictionaries, and ending with the symbol comprised in another one of the first sets of symbols the each of the dictionaries; selecting the identified fragment of the received sequence of symbols having the least number of symbols among the identified fragments of the received sequence of symbols; the selecting of the identified fragment of the received sequence of symbols having the least number of symbols among the identified fragments of the received sequence of symbols; and the selecting of the dictionary corresponding to the selected identified fragment of the received sequence of symbols is executed when the set of dictionaries comprises more than one of the dictionaries. The translating of the received sequence of symbols into the batch of commands parsable by the electronic controller of the electromechanical medical device comprises the following step: selecting the dictionary corresponding to the dictionary comprised in the set of dictionaries when the set of dictionaries consists of one of the dictionaries.

According to another embodiment, the translating of the received sequence of symbols into the batch of commands parsable by the electronic controller of the electromechanical medical device comprises the following step: generating an error of the translating of the received sequence of symbols into the batch of commands parsable by the electronic controller of the electromechanical medical device, when the set of dictionaries is an empty set or when two or more of the identified fragments of the received sequence of symbols have the same number of symbols being less than a number of symbols in any other, if any, identified fragment of the received sequence of symbols. The method comprises the following step: in response to the generating of the error aborting the translating of the received sequence of symbols into the batch of commands parsable by the electronic controller of the electromechanical medical device.

According to another embodiment, one of the first sets of symbols consists of symbols having synonym meaning.

According to another embodiment, each of the symbols of one of the first sets of symbols is a respective word of a natural language or a respective word combination of the natural language and all symbols of the one of the first sets of symbols are synonyms.

According to another embodiment, the received sequence of symbols is a phrase in a natural language.

According to another embodiment, each of the dictionaries has a respective order specification determining placing of symbols of its first sets of symbols in sequences of symbols.

For any of the dictionaries comprised in the set of dictionaries the symbols each comprised in the respective first set of symbols and in the received sequence of symbols are placed in the received sequence of symbols according to the respective order specification.

According to another embodiment, each of the order specifications complies with a syntax of a natural language.

According to another embodiment, each of the dictionaries comprises a respective maximum allowable number of symbols which can be placed between any of symbols of one of its first sets of symbols and any of symbols of another one of its first sets of symbols in sequences of symbols. For any of the dictionaries comprised in the set of dictionaries a respective number of symbols placed in the received sequence of symbols between two symbols between which the maximum allowable number of symbols is specified is less or equal to the respective maximum allowable number of symbols.

According to another embodiment, the received sequence of symbols is received from a user electronic interface device. Each of the batches of commands parsable by the electronic controller of the electromechanical medical device has a respective description. The method comprises the following steps: sending the description of the batch of commands of the selected dictionary to the user electronic interface device; the user electronic interface device receiving the description of the batch of commands of the selected dictionary; the user electronic interface device sending a communication signal to a user for communicating to the user the description of the batch of commands of the selected dictionary; the user electronic interface device receiving from the user a communication signal indicating that the description of the batch of commands of the selected dictionary corresponds to the received sequence of symbols; the user electronic interface device sending a confirmation message in response to the receiving the communication signal from the user; and receiving from the user electronic interface device the confirmation message. The sending the batch of commands from the control system to the electromechanical medical device and the causing by the electronic controller of the electromechanical medical device to execute the batch of commands on the electromechanical medical device is executed when the confirmation message is received from the user electronic interface device.

According to another embodiment, each of the batches of commands parsable by the electronic controller of the electromechanical medical device comprises one or more respective parameter fields. Each of the parameter fields is associated with respective second sets of symbols and the respective conversion rule for converting symbols into a respective format compatible with the each of the parameter fields. Each of some of the parameter fields is associated with a respective default parameter. The translating of the received sequence of symbols into the batch of commands parsable by the electronic controller of the electromechanical medical device comprises the following steps being executed for each of the parameter fields of the batch of commands of the selected dictionary when each criterion of a criteria set is compiled with: converting one or more symbols into the respective format using the conversion rule associated with the each of the parameter fields of the batch of commands of the selected dictionary, wherein each of the one or more symbols is comprised in the received sequence of symbols and in the respective second set of symbols associated with the each of the parameter fields of the batch of commands of the selected dictionary; and entering the one or more converted symbols in the each of the parameter fields of the batch of commands of the selected dictionary. The translating of the received sequence of symbols into the batch of commands parsable by the electronic controller of the electromechanical medical device comprises the following step being executed for each of the parameter fields of the batch of commands of the selected dictionary when at least one criterion of the criteria set is not compiled with: entering the respective default parameter associated with the each of the parameter fields of the batch of commands of the selected dictionary in the each of the parameter fields of the batch of commands of the selected dictionary when the each of the parameter fields of the batch of commands of the selected dictionary parameter field is associated with the respective default parameter, otherwise generating an error. The criteria set comprises the following criterion: each second set of symbols associated with the each of the parameter fields of the batch of commands of the selected dictionary comprises a respective symbol being comprised in the received sequence of symbols.

According to another embodiment, the control method comprises: in response to the generating of the error aborting the translating of the received sequence of symbols into the batch of commands parsable by the electronic controller of the electromechanical medical device.

According to another embodiment, each of the parameter fields is associated with a respective order specification determining placing of symbols of the second sets associated with it in sequences of symbols. The criteria set comprises the following criterion: the symbols each comprised in the respective second set of symbols associated with the each of the parameter fields of the batch of commands of the selected dictionary and in the received sequence of symbols are placed in the received sequence of symbols according to the order specification associated with the each of the parameter fields of the batch of commands of the selected dictionary.

According to another embodiment, each of the order specifications complies with a syntax of a natural language.

According to another embodiment, each of the parameter fields is associated with a respective maximum allowable number of symbols which can be placed between any of symbols of one of the second sets of symbols associated with it and any of symbols of another one of second sets associated with it in sequences of symbols. The criteria set comprises the following criterion: a number of symbols placed in the received sequence of symbols between two symbols between which the maximum allowable number of symbols is specified is less or equal to the maximum allowable number of symbols associated with the each of the parameter fields of the batch of commands of the selected dictionary.

According to another embodiment, the received sequence of symbols is received from a user electronic interface device. Each of the batches of commands parsable by the electronic controller of the electromechanical medical device has a respective description. Each of the parameter fields has a respective description. The method comprises the following steps being executed when either the one or more respective converted symbols or the respective default parameter is entered in each of the parameter fields of the batch of commands of the selected dictionary: generating a message comprising the description of the batch of commands of the selected dictionary, the description of each of the parameter fields of the batch of commands of the selected dictionary and either the one or more respective converted symbols or the respective default parameter being entered therein; sending the message to the user electronic interface device; the user electronic interface device sending to a communication signal to a user for communicating to the user the message; the user electronic interface device receiving from the user a communication signal indicating that the description of the batch of commands of the selected dictionary corresponds to the received sequence of symbols and the parameter fields of the batch of commands of the selected dictionary are filled in correctly; the user electronic interface device sending a confirmation message in response to the receiving the signal from the user; receiving from the user electronic interface device the confirmation message. The sending the batch of commands from the control system to the electromechanical medical device and the causing by the electronic controller of the electromechanical medical device to execute the batch of commands on the electromechanical medical device is executed when the confirmation message is received from the user electronic interface device.

According to another embodiment, the control method comprises the following steps being executed before execution of said steps which are executed for the each of the parameter fields of the batch of commands of the selected dictionary: generating an auxiliary set of symbols, wherein a number of symbols in the another auxiliary set is equal to a number of the first sets in the selected dictionary, wherein each of the symbols comprised in the auxiliary set is comprised in one of the first dictionaries of the selected dictionary and in the received sequence of symbols; and deleting each symbol of the auxiliary set from the received sequence of symbols.

FIG. 1 illustrates an example environment for controlling a set of electromechanical medical devices 111, 112, 113, wherein each of the electromechanical medical devices 111-113 of the set can have a can have an assigned identification information for identifying of the each electromechanical medical device (e.g. an identification number, IP address, or a name). Specifically, the illustrated environment includes a control system 140. The control system 140 can comprise the following components: one or more I/O ports 141, 142, a database 143, a computer processor 144 controlling the control system 140, a memory 145, and one or more data buses providing communicative coupling of these and other components of the control system 140. The I/O port 141 is communicatively coupled to an electronic controller 111a of the electromechanical medical device 111 via computer network 161. The I/O port 141 is communicatively coupled to an electronic controller 112a of the electromechanical medical device 112 via computer network 161. The I/O port 142 is communicatively coupled to an electronic controller 113a of the electromechanical medical device 113 via computer network 162. The network 161 can be a wired network e.g. Ethernet or a wireless network e.g. WiFi. The network 162 can be a wired or a wireless network. The control system can be communicatively coupled to one or more user electronic interface devices 160 via one or more computer networks 163. One or more of these computer networks can be implemented using digital cellular telecommunication networks. At least two of the networks 161-163 can be the same computer network. The user electronic interface device can be a computer, a handheld computer device, or any other electronic device having a functionality of a user interface.

The control system is configured to receive sequences of symbols, translate them in batches of commands parsable by the electronic controllers of the electromechanical medical devices, and cause the electronic controllers to execute the batches of commands on the respective electromechanical medical devices. The sequences of symbols can comprise a one or more words, and/or one or more word combinations, and/or one or more icons, and/or one or more combinations of icons, and/or one or more pictograms, and/or one or more combinations pictograms, and/or one or more graphical images, and/or one or more combinations of graphical images, and/or one or more numbers, and/or one or more combinations of numbers. The sequences of symbols can have at least some symbols ordered therein according to a syntax of a natural language. This broad spectrum of symbols which can be processed by the control system 140 can enable receiving of instructions from a broad spectrum of user electronic interface devices supporting different user interfaces and data exchange protocols for communicating with the control system 140. For instance, the sequence of symbols can be an E-Mail message sent from a user electronic interface device to the control system 140. The sequence of symbols can be a text message or/and a combination of icons received via a program supporting such a communication such as for instance "Skype" or "WhatsApp" messenger. The sequence of symbols can be generated by the user electronic interface device by converting a human speech into the sequence of symbols (e.g. words, and/or word combinations, and/or numbers, and/or combination of numbers) using speech recognition software.

The database 143 can store batches of commands parsable by electronic controllers of electromechanical medical devices, and/or technical data (e.g. dictionaries) for identification of the batch of commands corresponding to a sequence of symbols (or a fragment of it) received by the control system 140, and/or technical data enabling identification of the device, and/or parameter values for entering in parameter fields of commands of the batches of commands.

The database 143 can comprise technical data for identifying data in a sequence of symbols and entering it into parameter fields of commands or batches of commands. The technical data can comprise conversion rules for converting the identified data into formats compatible with parameter fields.

The memory 145 stores instructions of a computer executable code which execution by the computer processor 144 causes the control system 140 to perform one or more control methods described herein.

Figure 2:
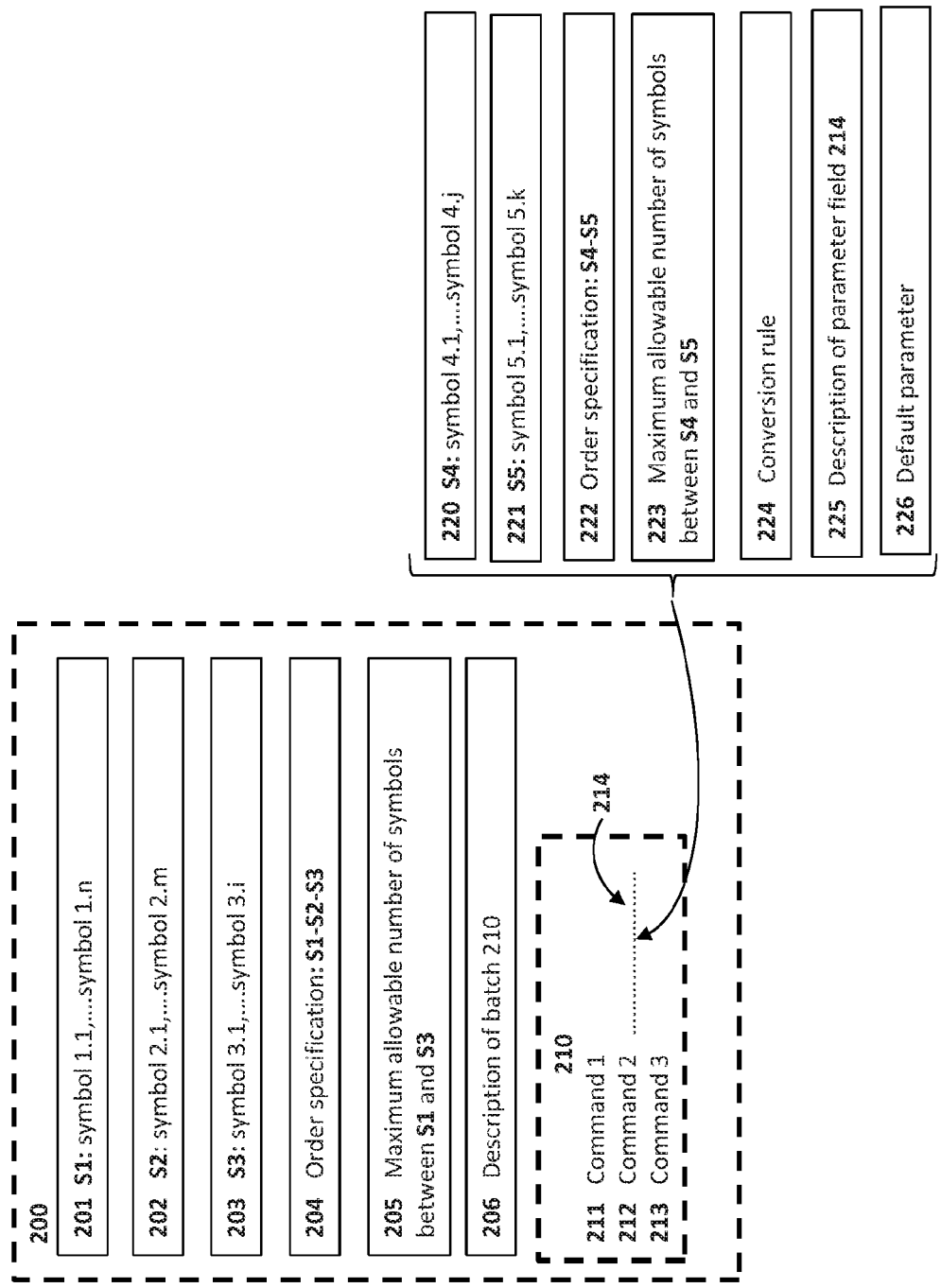
FIG. 2 shows a data structure of a dictionary and related information.

Each dictionary has a respective batch of commands parsable by an electronic controller of the electromechanical medical device and respective sets of symbols corresponding to the respective batch of commands of the each dictionary. Each of the sets comprises at least one respective symbol. The batch of commands of a particular dictionary is used as a translation of the sequence of symbols when each set of said dictionary comprises one symbol being comprised in the sequence of symbols. This criterion can be formulated in a more rigorous way. The batch of commands of a particular dictionary is used as a translation of the sequence of symbols when each set of said dictionary comprises only one symbol being comprised in the sequence of symbols. The aforementioned criteria and the sets of symbols are comprised in the technical data for identification of the batch of commands corresponding to a sequence of symbols. FIG. 2 depicts an example dictionary 200 for translating symbols comprised in sequence of symbols into a batch 210 of commands 211-213. The dictionary comprises 3 sets of symbols 201-203. Thus when the batch of commands 210 is a translation of a sequence of symbols, when the sequence of symbols comprises one symbol of set S1 201 (e.g. symbol 1.1), one symbol of set S2 201 (e.g. symbol 2.1), and one symbol of set S3 203 (e.g. symbol 3.1). In another case, when the sequence of symbols does not comprise any of symbols of one of the sets (e.g. S2 202), then the batch of commands 210 is not a translation of the sequence of symbols.

For each of some of the sets of symbols the following constraint can be valid: the set of symbols consist of symbols having synonym meaning, wherein each of the symbols of the set can be a respective word of a natural language or a respective combination of words of the natural language. This constraint is of particular importance when the sequence of symbols is or comprises one or more phrases of a natural language. The synonym meaning of symbols can be determined by their meaning in a particular language and/or by their meaning in context of particular application.

The selection of a particular batch of commands using the dictionaries can be illustrated on the following example, wherein a sequence of symbols comprises the following phrase: "activate tool Alpha" and the database stores a dictionary comprising a batch of commands for activation of the tool Alpha". Each word of the phrase has a synonym in the English language and/or a synonym determined by an application context. For instance one device can have different names. Thus in order to translate the phrase into the correct batch of commands, the dictionary has to comprise three sets of synonyms. The first set can comprise the following: "activate", "ramp-up", "switch on", "turn on". The second set can comprise the following: "device", "tool", "system", "apparatus". The third set can comprise different names of the tool such as "Alpha", "XYZ", "Gamma-Knife". It should be understood, that these sets are just examples, because the lists of synonyms can be broader or smaller depending on particular language and context of particular application. The batch of commands is selected as a translation of the sequence of symbols not only when it comprises the aforementioned phrase, but other phrases formulated using any other words of each set, e.g. the sequence of symbols can comprise one of the following phrases: "turn on device Gamma-Knife", "switch on tool Alpha", "ramp-up apparatus Alpha", etc.

Determination whether a particular symbol is comprised in a set can be based not only on a match of the particular symbol with of one of the symbols of the set as mentioned above but on a compliance criteria. The symbol can be a number which can be formulated in different formats. For instance, a number 0.1 can be formulated as 1e-1 or 1.0e-1. In this case the criterion for a symbol being comprised in a set can be formulated as an interval. For instance, any symbol representing a number can be comprised in a set when the number is within a specified interval, e.g. the symbol being a number 0.1 is comprised in a set comprising only numbers consisting of numbers being bigger than zero and less than one.

The dictionary can have one or more criteria to be complied with for using the batch of commands of this dictionary as a translation of a sequence of symbols. One of the criteria is order specification determining placing of symbols of its sets in sequences of symbols. For instance when a dictionary has 3 sets of symbols S1, S2, S3 then the criterion can be formulated as follows: any symbol of set S2 has to be placed in the sequence of symbols between any symbol of set S1 and any symbol of set S3. The order specification can specify more than one variant of placing of symbols of sets of the dictionary in sequences of symbols. For instance the aforementioned criterion can be formulated as follows: any symbol of set S2 has to be placed in the sequence of symbols between any symbol of set S1 and any symbol of set S3 or any symbol of set S3 has to be placed in the sequence of symbols between any symbol of set S2 and any symbol of set S1. The example dictionary of 200 on FIG. 2 has the order specification 204 S1-S2-S3 meaning that any symbol of set S2 has to be placed in the sequence of symbols between any symbol of set S1 and any symbol of set S3. Application of this criterion can improve reliability of translation of sequences of symbols by filtering out combinations of symbols formulated in an ambiguous and/or incorrect way.

The order specification can comply with a syntax of a natural language. This can be illustrated on the aforementioned example related to the selection of the batch of commands for the activation of the tool Alpha. According the syntax of the English language the criterion can be formulated as follows: any of the words of the second set has to be placed in a phrase or its fragment between any of the words of the first set and any of the words of the third set or any of the words of the third set has to be placed in a phrase or its fragment between any of the words of the first set and any of the words of the second set. The phrases "activate tool Alpha" and "activate Alpha tool" comply with the criterion, while phrases "tool Alpha activate" or "Alpha tool activate" do not comply with the criterion.

Another one of the aforementioned criteria to be complied with is a specification of a maximum allowable number of symbols which can be placed in sequences of symbols between any of symbols of one of the sets of a particular dictionary and any of symbols of another one of the sets of the particular dictionary. The dictionary can have more than one maximum allowable number symbols, wherein each of the maximum allowable number of symbols is specified for different pairs of its sets. This criterion can be illustrated on the following example, wherein the sequence of symbols consists of the following sequence of symbols: Symbol 1, Symbol 2, Symbol 3, Symbol 4. Symbol 1 is comprised in one of the sets of a dictionary and Symbol 4 is comprised in another one of the sets of the dictionary. There are two symbols (Symbol 3 and Symbol 2) placed in the sequence of symbols between two different symbols (Symbol 1 and Symbol 4) each being comprised in the respective set. When the maximum allowable number of symbols is one, then the criterion is not complied with. When the maximum allowable number of symbols is two, then the criterion is complied with. Application of such criteria can improve reliability of translation of sequences of symbols by filtering out combinations of symbols formulated in an ambiguous and/or incorrect way.

Application of such criteria can be illustrated on the aforementioned example related to the activation of the tool Alpha. In this case the sequence of symbols is formulated as follows: "activate the device which was repaired yesterday and start maintenance of Alpha." The sequence of symbols comprises symbols "activate device Alpha", each comprised in the respective set of the dictionary. Moreover the symbols are placed in the sequence of symbols in a correct way, i.e. their placing complies with the order specification. However, the sequence of symbols does not comprise an instruction to activate the tool Alpha. The error of translation can be avoided when a maximum number of symbols in sequences of symbols between any symbol (word) of the first set and any symbol (word) of the third set is specified. When the maximum allowable number of symbols is set to one, this phrase will not be translated into the batch of commands for the activation of the tool Alpha. Moreover, all other aforementioned correct example sequences of symbols (phrases) will be still translated in the batch of commands for the activation of the tool Alpha. The example dictionary 200 depicted on FIG. 2 has one criterion 205 determining a maximum allowable symbols placed in sequences of symbols between any of symbols of set S1 201 and any of symbols of set S3 203.

In addition, the batch of commands can have its description. The batch of commands 210 of the example dictionary 200 depicted on FIG. 2 has a respective description 206. The database 143 can store one or more of the aforementioned criteria for using the dictionary (e.g. 204, 205) and/or description of its batch of commands (e.g. 206) each as separate data item being associated with the dictionary. Alternatively, the dictionary (e.g.) can comprise one or more of the aforementioned criteria of using the dictionary and/or the description of its batch of commands. The database can store a plurality of dictionaries, each having a respective batch of commands and respective sets. In addition each of the dictionaries can have a respective order specification, and/or one or more maximum allowable numbers of symbols, and/or description of its batch.

As it is mentioned above the batch of commands can have one or more parameter fields for entering data comprised in the sequence of symbols. Some of the parameter fields can have respective default parameters (or default parameter values) to be entered therein when no data for entering into the respective parameter field is comprised in the sequence of symbols. In the example depicted on FIG. 2 the batch 210 of commands 211-213 of the dictionary 200 has one parameter field 214 having default parameter 226.

Each of the parameter fields has one or more respective sets of symbols, each comprising at least one symbol. The sets of symbols can be stored in the database 143. The sets of symbols are used in a similar way for identification of data in a sequence of symbols to be entered in the respective parameter field. When each of the sets of symbols associated with the parameter field comprises one symbol being comprised in the sequence of symbols then the sequence of symbols comprises data for entering in the parameter field. This criterion can be formulated in a more rigorous way: when each of the sets of symbols associated with the parameter field comprises only one symbol being comprised in the sequence of symbols then the sequence of symbols comprises data for entering in the parameter field. Another constraint can be added to any of these criteria. At least one symbol comprised in the respective set of the dictionary comprising the batch of commands having said parameter field and in the sequence of symbols is not any of the symbols each of which is comprised in the respective set associated with said parameter field and in the sequence of symbols.

Each of the parameter fields can have a respective conversion rule. The conversion rules can be stored in the database 143. The conversion rule is used for converting one or more symbols into a format compatible with the respective parameter filed. The parameter fields can have different formats of data to be entered therein. The conversion rule is used when the aforementioned criterion is complied with, i.e. when a sequence of symbols comprises data to be entered into a respective parameter filed. The conversion rule is used for converting one or more symbols, wherein each of the one or more symbols is comprised in the respective set of symbols associated with the parameter filed and in the sequence of symbols. In addition the conversion rule can specify symbols of which sets associated with the parameter field are to be converted. For instance, the parameter filed 214 depicted on FIG. 2 has two associated symbol sets S4 220 and S5 221 and an associated conversion rule 224. The conversion rule can specify that only any of symbols of set S5 when comprised in the sequence of symbols is to be converted using the conversion rule.

When the aforementioned criterion is complied with (i.e. when a sequence of symbols does not comprise data to be entered into a respective parameter filed) and there is a default parameter (or a default parameter value) associated with the parameter field, then it can be entered in the parameter filed. The default parameters (or default parameter values) can be stored in the database 143. The parameter field 214 depicted on FIG. 2 has the respective default parameter 226.

An additional criterion can be used for determining whether a sequence of symbols comprises data to be entered in a parameter field. The additional criterion is an order specification determining placing of symbols of sets associated with the parameter field in sequences of symbols. This criterion and compliance with it are formulated in the same way as the aforementioned criterion related to order specification determining placing of symbols of sets of the dictionary in sequences of symbols. The parameter field 214 depicted on FIG. 2 has the respective order specification 222 determining that any of symbols of set S4 has to be placed in a sequence of symbols before any of symbols of set S5.

Yet another additional criterion can be used for determining whether a sequence of symbols comprises data to be entered in a parameter field. The another additional criterion is a specification of a maximum allowable number of symbols which can be placed in sequences of symbols between any of symbols of one of the sets associated with a parameter field and any of symbols of another one of the sets associated with the same parameter field. One parameter field can have more than one maximum allowable number of symbols, wherein each of the maximum allowable number of symbols is specified for a different pairs of sets. This criterion and compliance with it are formulated in the same way as the aforementioned criterion related to the maximum allowable number of symbols which can be placed in sequences of symbols between any of symbols of one of the sets of a dictionary and any of symbols of another one of the sets of the same dictionary. The parameter field 214 depicted on FIG. 2 has the respective order specification 223 determining a maximum allowable number of symbols placed in sequences of symbols between any symbol of set S4 and any of symbols of set S5.

Each parameter field can have its respective description. The parameter field 214 depicted on FIG. 2 has the respective description 225. The descriptions and/or the formulations of the aforementioned criteria can be stored in the database 143.

A process of entering data in a parameter filed can be illustrated on the following example. In this example a sequence of symbols comprises the following phrase: "acquire X-Ray image using source Alpha". This phrase consists of two fragments "acquire X-Ray image" and "using source Alpha". The fragment "quire X-Ray image" can be processed as described above, wherein a result thereof a batch of commands for acquisition of the X-Ray image" is selected. This batch of commands has a parameter field for entering a source identification of a source to be used for acquisition of X-Ray images. The parameter field has 3 sets of symbols. The first set of symbols comprises the following words: "using", "employing". The second set of symbols comprised the following words: "source", "device", "component", "unit". The third set of symbols comprises the following words: "Alpha", "Beta", "Gamma". Each of these sets comprises a respective word comprised in the phrase. In addition it is assumed that placing of words in the fragment "using source Alpha" complies with other aforementioned criteria related to order specification and maximum allowable number of symbols between one or more pairs of the sets associated with the parameter field. Thus the phrase comprises data for entering into the parameter field. The conversion rule associated with the parameter field specifies that a symbol comprised in the third set and in the sequence of symbols is to be converted into a format compatible with the parameter field, wherein a parameter value "1" is to be entered in the parameter field when a symbol comprised in the third set and in the sequence of symbols is "Alpha", wherein a parameter value "2" is to be entered in the parameter field when a symbol comprised in the third set and in the sequence of symbols is "Bet", wherein a parameter value "3" is to be entered in the parameter field when a symbol comprised in the third set and in the sequence of symbols is "Gamma". Since the word "Alpha" is comprised in the third set and in the sequence of symbols the parameter value "1" is entered in the parameter field. In case when the fragment "using source Alpha" is missing in the sequence of symbols, then a default parameter value "1" is entered in the parameter field.

Figure 3:
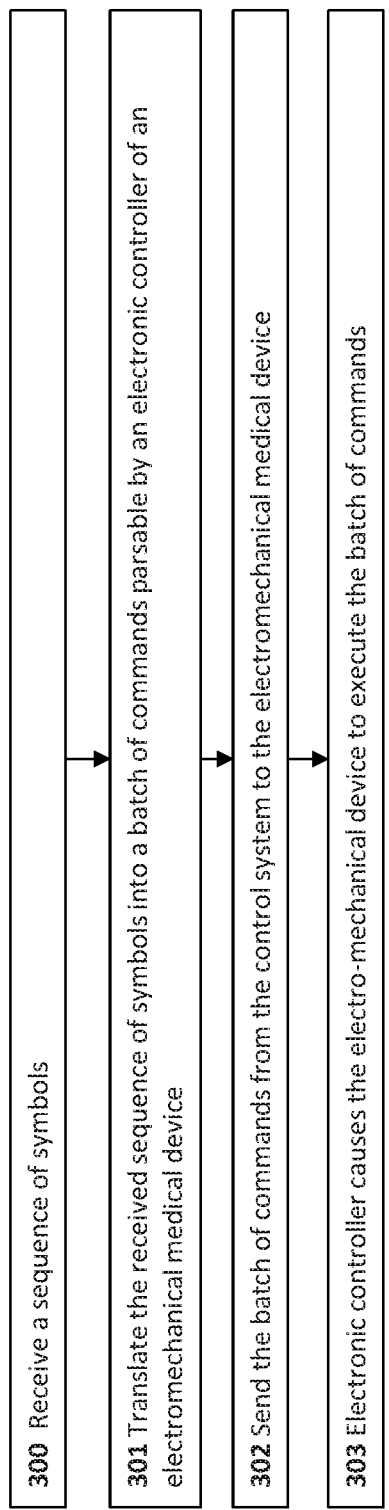
FIG. 3 shows a flowchart of an example method.

The control method depicted on FIG. 3 begins with process block 300. In the process block 300 the control system receives a sequence of symbols. The sequence of symbols can be received from the user electronic interface device. Process block 301 is executed after process block 300. In process block 301 the control system translates the received sequence of symbols into a batch of commands parsable by an electronic controller of an electromechanical medical device. Process block 302 is executed after process block 301. In process block 302 the batch of commands is sent from the control system to the electromechanical medical device. After receiving of the batch of commands the electronic controller causes the electromechanical medical device to execute the batch of commands in process block 303.

Figure 4:
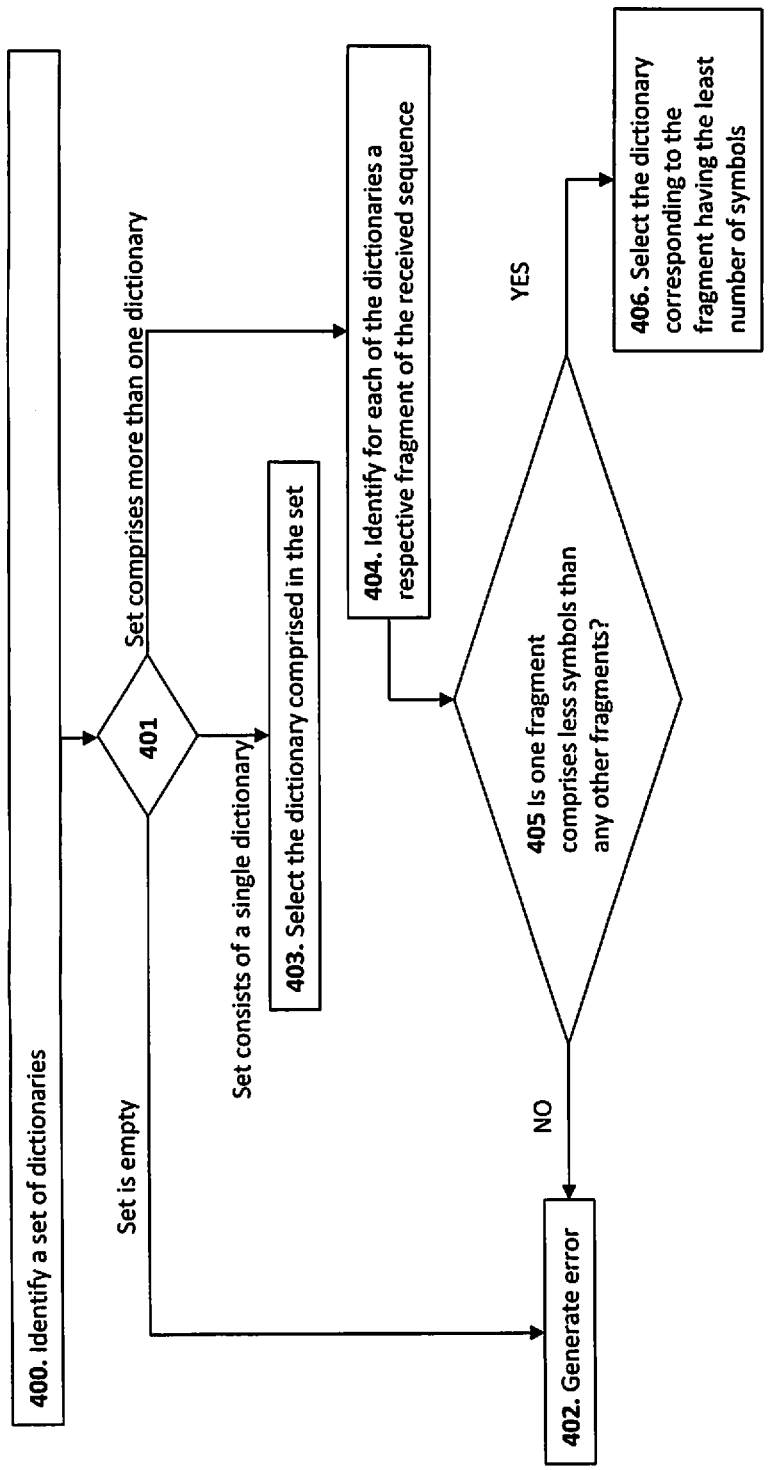
FIG. 4 shows a flowchart of an example method.
Figure 5:
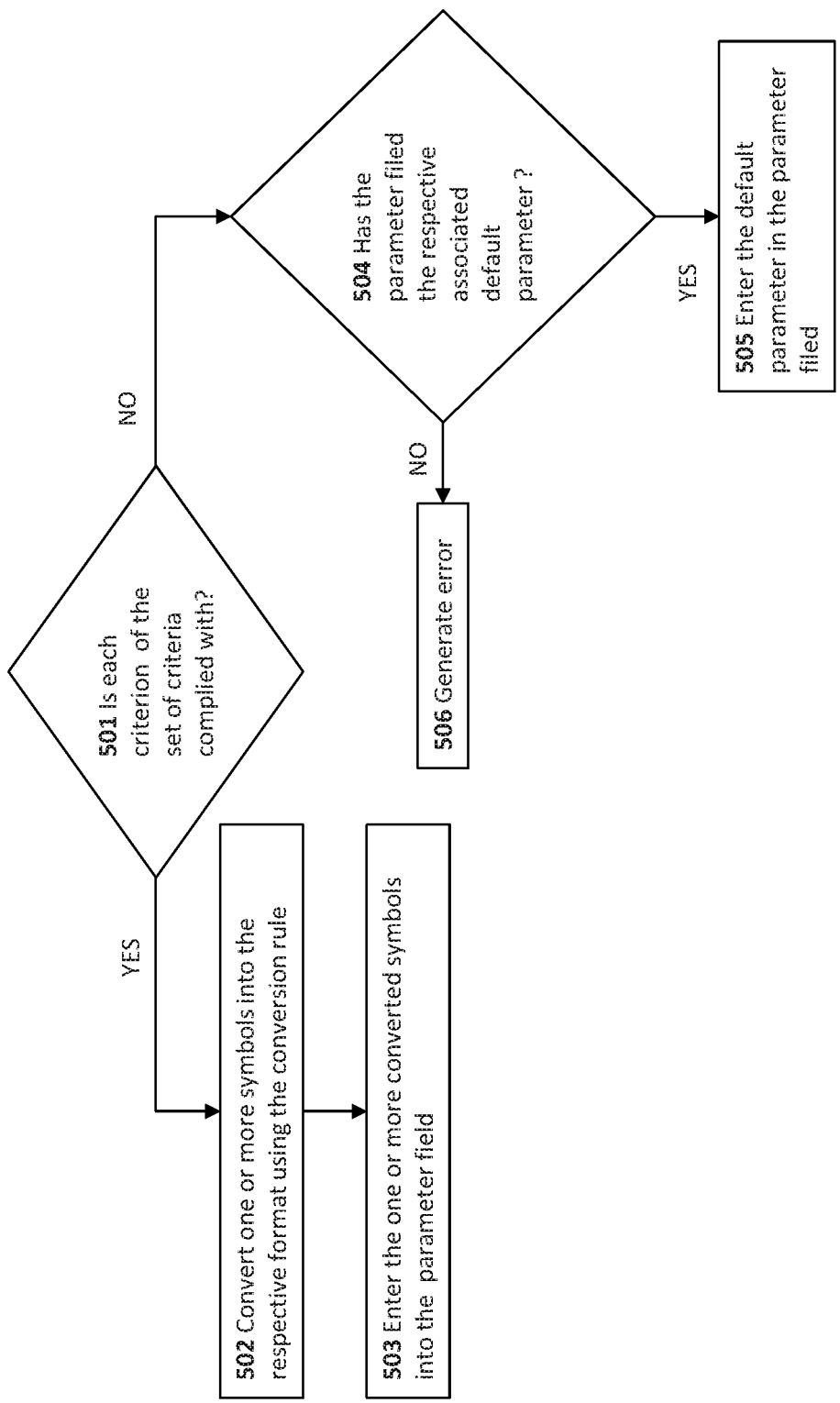
FIG. 5 shows a flowchart of an example method.
Figure 6:
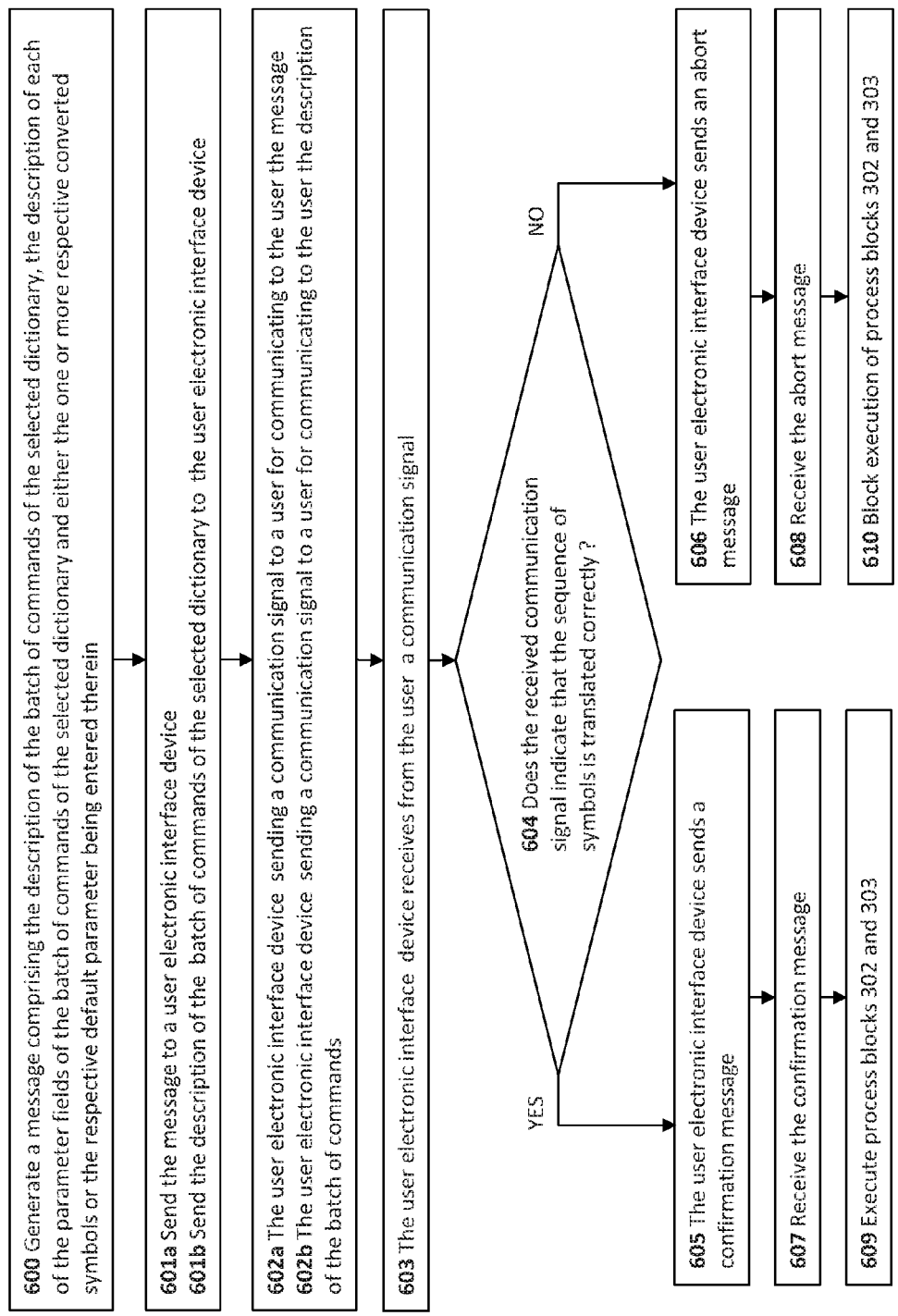
FIG. 6 shows a flowchart of an example method.

Process block 301 can comprise one or more process blocks depicted on FIGS. 4-6. FIG. 4 depicts a flowchart diagram for selecting a batch of commands on a basis of data comprised in the sequence of symbols, which can be received in process block 300. The method begins with process block 400 in which a set of dictionaries is selected. Each of the dictionaries of the set complies with the following constraint formulated above: each set of the dictionary comprises one symbol comprised in the sequence of symbols. As it is mentioned above more rigorous aforementioned constraint can be applied: each set of the dictionary comprises only one symbol comprised in the sequence of symbols. The rigorous formulation of the constraint enables exclusion of ambiguous cases when one set of one of the dictionaries of the set comprises more than one symbol being comprised in the sequence of symbols. For instance, the sequence of symbols can comprise the following phrase: "activate tool Omega and tool Alpha is to be switched off". The dictionary comprising a batch for activation of the tool Alpha comprises three sets of symbols, the first set comprises the word "activate", the second set comprises the word "tool", the third set comprises the word "Alpha". The word "tool" is comprised twice. When the rigorous criterion is not applied the sequence of symbols is erroneously translated in the batch of commands for the activation of the tool Alpha because it comprises words "activate", "tool", and "Alpha". When the rigorous criterion is applied the erroneous translation is not possible.

Further one or more of the aforementioned criteria can be applied for the selection of dictionaries of the set in process block 400. For instance the aforementioned criterion related to order specification (e.g. order specification 204 on FIG. 2). can be applied for the selection of the dictionaries. Another criterion for selection dictionaries of the set, can be the aforementioned criterion related to the maximum allowable number of symbols in sequences of symbols between symbols of different sets of a dictionary (e.g. maximum allowable number of symbols 205 in sequences of symbols between any symbol of set S1 and any symbol of set S3 (FIG. 2)).

Decision process block 401 is executed after process block 400. Decision process block 401 causes execution of process block 402 when the set is empty. Decision process block 401 causes execution of process block 403 when the set consists of only one dictionary. Decision process block 401 causes execution of process block 404 when the set comprises more than one dictionary. As it will be clear from the following description, the branch of the decision process block causing execution of process block 403 and the process block 403 are optional. The result of execution of the method depicted on FIG. 4 will be exactly the same when this branch and process block are not used, but it might take more time and/or computer resources.

In process block 404 for each of the dictionaries of the set a respective fragment of the sequence of symbols is identified. The fragment of the sequence of the each of the dictionaries comprises one symbol of each of the sets of the each of the dictionaries. The length of the fragment is determined according to the following constraint: each fragment begins with a symbol comprised in the respective set of a dictionary and ends with a symbol comprised in another set of the same dictionary. In case when for one of the dictionaries the selection of the respective fragment can be done in several ways, then the fragment having the least number of symbols is selected for the one of the dictionaries. The latter can be illustrated on the following example, wherein the sequence of symbols is the following one: Symbol 1, Symbol 2, Symbol 3, Symbol 4. An example dictionary has two sets of symbols. Symbol 1 and Symbol 4 are comprised one of the sets, while Symbol 3 is comprised in another one of the sets. The example sequence of symbols has two fragments, each comprising one symbol of one of the sets and one symbol of another one of the sets. One of the fragments is: Symbol 1, Symbol 2, Symbol 3. Another one of the fragments is: Symbol 3, Symbol 4. In this example, the latter fragment is selected because it comprised less symbols.

Decision process block 405 is executed after process block. Decision process block 405 causes execution of process block 402 when there is only one of the identified fragments which has less symbols than any other of the identified fragments, otherwise it causes execution of process block 406. Decision process block 405 can provide unambiguous translation of the received sequence of symbols, because it provides for a single dictionary selected in process block 406 when the latter is executed.

In process block 406 the dictionary corresponding to the fragment having the least number of symbols among the identified in process block 404 fragments of the sequence of symbols is selected.

In process block 403 the dictionary of the set of dictionaries is selected.

The batch of commands of the dictionary selected in process block 403 or process block 406 is the one which is generated in process block 301, i.e. the one being the translation of the received sequence of symbols.

In process block 402 an error is generated. In repose to the generating of error execution of process block 301 is aborted and as a result thereof subsequent process blocks 302 and 303 are not executed. In response to the aborting of the execution of process block 301 an error message can be sent to a user electronic interface device from which the sequence of symbols is received. In response to receiving of the error message, the user electronic interface device can send to a user a signal indicating that the sequence of symbols cannot be translated into a batch of commands.

The functioning of decision process 405 block and the next following process block 406 is of particular importance when the sequence of symbols is very long and several dictionaries are selected in the set of dictionaries. The functionality of these process blocks can be illustrated on the following example, wherein the received sequence of symbols is the following phrase: "activate tool Omega and acquire X-Ray image using tool Beta". In this example there are only two dictionaries. One dictionary comprises a batch of commands for activation of the tool Beta, a first set comprising "activate", a second set comprising "tool", a third set comprising "Beta". Another dictionary comprises a batch for acquisition of the X-Ray image, a fourth set comprising "acquire", and a fifth set comprising "X-Ray" image. Both of the dictionaries are comprised in the set of dictionaries because each of their sets comprises symbol comprised in the sequence of symbols. However, their symbols are comprised in respective fragments of the sequence of symbols having different lengths. The symbols of the sets of the dictionary comprising the batch of commands for activation of the tool Beta are comprised the following fragment "activate tool Omega and acquire X-Ray image using tool Beta". The symbols of the sets of the dictionary comprising the batch of commands for acquisition of the X-Ray image is comprised in the following fragment: "acquire X-Ray image". Since the latter fragment comprises less symbols the correct dictionary is used for translation of the sequence of symbols in process block 406.

As it is mentioned above, a batch of commands can comprise one or more parameter fields. Data for entering in the parameter field can be comprised in the sequence of symbols. Some of the parameter fields can have respective default parameters for entering therein. FIG. 5 depicts a flowchart of a method for filling in the parameter fields of a batch of commands. This method can be comprised in process block 301. The method depicted on FIG. 5 is executed for each of the parameter fields of the batch of commands. The batch of commands can be the one of the dictionary selected in process block 403 or process block 406.

An optional process block can be executed before execution of the method depicted on FIG. 5 for any of the parameter fields. In this process block an auxiliary set of symbols is generated. Each of the symbols of the auxiliary set is comprised in the received sequence of symbols and in the respective set of the dictionary comprising the batch of commands which parameter fields have to be filled in. A number of symbols in the auxiliary set is equal to a number of sets of the dictionary. After generation of the auxiliary set, each of its symbols is deleted from the received sequence. This procedure can facilitate identification in the received sequence of data to be field in the parameter filed because the received sequence of symbols comprises less symbols after execution of the optional process block and as a result thereof the volume of information in which the data to is to be identified is reduced.

The method depicted on FIG. 5 begins with a decision process block 501. Decision process block 501 causes execution of process block 502 when each criterion of the set of criteria is complied with, otherwise it causes execution of decision process block 504. The set of criteria comprises the following aforementioned criterion: each set of symbols (e.g. S4 and S5 on FIG. 2) associated with the parameter field (e.g. 214 on FIG. 2) for which the method on FIG. 5 is executed comprises a respective symbol being comprised in the received sequence of symbols. The set of criteria can comprise another aforementioned criterion related to the order specification of symbols of the sets of symbols associated with the parameter field for which the method on FIG. 5 is executed (e.g. order specification 222 on FIG. 2). The set of criteria can comprise yet another aforementioned criterion related to the maximum allowable number of symbols in sequences of symbols between symbols of different sets associated with the parameter field for which the method on FIG. 5 is executed (e.g. maximum allowable number of symbols 223 in sequences of symbols between any symbol of set S4 and any symbol of set S5 (FIG. 2)).

In process block 502 one or more symbols are converted into the format using the conversion rule (e.g. 224 on FIG. 2) associated with the of the parameter field for which the method of FIG. 5 is executed. Details of conversion are described above. Each of the one or more symbols is comprised in the received sequence of symbols and in the respective set of symbols associated with the parameter field for which the method of FIG. 5 is executed.

Process block 503 is executed after process block 502. In process block 503 the one or more symbols converted into the parameter field for which the method of FIG. 5 is executed.

Decision process block 504 causes execution of process block 505 when the parameter field for which the method depicted on FIG. 5 is executed has an associated default parameter (or default parameter value) (e.g. default parameter 226 associated with parameter field 214 on FIG. 214), otherwise it causes execution of process block 506.

In process block 505 the default parameter (or the default parameter value) associated with the parameter field for which the method depicted on FIG. 5 is executed is entered in this parameter filed.

In process block 506 an error is generated. In repose to the generating of error execution of process block 301 is aborted and as a result thereof subsequent process blocks 302 and 303 are not executed. In response to the aborting of the execution of process block 301 an error message can be sent to a user electronic interface device from which the sequence of symbols is received. In response to receiving of the error message, the user electronic interface device can send to a user a signal indicating that the sequence of symbols cannot be translated into a batch of commands.

FIG. 6 depicts a flowchart of a method providing confirmation of a translation of the received sequence of symbols into the batch of commands. As it is mentioned above, the batch of commands (e.g. 210) can have its description (e.g. 206) and its one or more parameter fields (e.g. 214) each can have its respective description (e.g. 225) as well. This information in combination with data, if any, entered in the parameter fields or a portion of it can be sent to a user electronic interface device (e.g. 160) for the confirmation of the translation.

The method which flowchart depicted on FIG. 6 begins with an optional process block 600. In process block 600 a message is generated. The message comprises at least one of the following: a description of the batch of commands being a translation of the received in process block 300, one or more description of the parameter fields, if any, of the batch of commands and respective data entered therein. As mentioned above the data entered in the parameter filed can be one or more converted symbols or a default parameter (or a default parameter value). Process block 601a is executed after process block 600. In process block 601a the message is sent to a user electronic interface device. The user electronic device can be the one from which the sequence of symbols is received in process block 300. In case when process block 600 is not executed, the method begins with process block 601b. In process block 601b the description of the batch of commands is sent to the user electronic interface device.

Process block 602a is executed after process block 601a. In process block 602a, in response to receiving the message the user electronic interface device sends a communication signal to a user for communicating to the user the message. The communication signal can be displaying on a screen of the user electronic interface device of the message. Alternatively or in addition the communication signal can be an audio signal comprising content of the message.

Process block 602b is executed after process block 601b. In process block 602b, in response to receiving the description of the batch of commands the user electronic interface device sends a communication signal to a user for communicating to the user the description of the batch of commands. The communication signal can be displaying on a screen of the user electronic interface device of the description of the batch of commands. Alternatively or in addition the communication signal can be an audio signal comprising content of the description of the batch of commands.

Process block 603 is executed either after process block 602a or after process block 601b. In process block 603 the user electronic device receives from the user a communication signal. The sequence of symbols can be received from the same user via the same user electronic interface device.

Decision process block 604 causes execution of process block 605 when the received in process block 603 communication signal indicates that the received sequence of symbols is translated into the batch of commands in a correct way, otherwise it causes execution of process block 606. In case, when only the description of the batch of commands is sent to the user electronic interface device (i.e. process block 602b is executed) the received signal can indicate whether the description of the batch of commands corresponds to the received sequence of symbols. When this statement is true, then decision process block 604 causes execution of process block 605, otherwise it causes execution of process block 606.

In case when process block 601 is executed, the received signal can indicate whether that the description of the batch of commands of the selected dictionary corresponds to the received sequence of symbols and the parameter fields of the batch of commands of the selected dictionary are filled in correctly, i.e. the respective converted one or more symbols are correct and/or the respective default parameter (or the respective default parameter value) is correct. When this statement is true, then decision process block 604 causes execution of process block 605, otherwise it causes execution of process block 606.

In process block 605 the user electronic interface device sends a confirmation message to the control system. Process block 607 is executed after process block 605. In process block 607 the control system receives the confirmation message. Process block 609 is executed after process block 607. In process block 609 process blocks 302 and 303 are executed. Alternatively, in process block 609 execution of process blocks 302 and 303 is enabled.

In process block 606 the user electronic interface device sends an abort message to the control system. Process block 608 is executed after process block 606. In process block 608 the control system receives the abort message. Process block 610 is executed after process block 608. In process block 610 execution of process blocks 302 and 303 is blocked. Alternatively or in addition, execution of process block 301 is aborted.

The preceding figures and accompanying description illustrate the example processes and computer implementable techniques. But example environment (or their software or other components) contemplate using, implementing, or executing any suitable technique for performing these and other tasks. It will be understood that these processes are for illustration purposes only and that the described or similar techniques may be performed at any appropriate time, including concurrently, individually, in parallel, and/or in combination. In addition, many of the operations in these processes may take place simultaneously, concurrently, in parallel, and/or in different orders than as shown. Moreover, the example environment may use processes with additional, fewer and/or different operations, as long as the methods remain appropriate.

In other words, although this disclosure has been described in terms of certain implementations and generally associated methods, alterations and permutations of these implementations and methods will be apparent to those skilled in the art. Accordingly, the above description of example implementations does not define or constrain this disclosure. Other changes, substitutions, and alterations are also possible without departing from the spirit and scope of this disclosure.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The term "control system" refers to data processing hardware and encompasses all kinds of apparatus, devices, and machines for processing data, including by way of example, a programmable processor, a computer, or multiple processors or computers. The apparatus can also be or further include special purpose logic circuitry, e.g., a central processing unit (CPU), a FPGA (field programmable gate array), or an ASIC (application specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a FPGA, or an ASIC.

Computers suitable for the execution of a computer program can be based on general or special purpose microprocessors, both, or any other kind of CPU. Generally, a CPU will receive instructions and data from a read only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically-erasable programmable read-only memory (EEPROM), and flash memory devices; magnetic disks, e.g., internal hard disks or removable disks; magneto optical disks; and CD ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

The "electronic user interface" may be a "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back end component, e.g., as a data server, or that includes a middleware component, e.g., an application server, or that includes a front-end component, e.g., a client computer having a graphical user interface or a web browser through which a user can interact with an implementation of the subject matter described in this specification, or any combination of one or more such back end, middleware, or front end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any implementation or on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some causes be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

The invention claimed is:

1. A control method for controlling an electromechanical medical device, the method comprising:
   receiving, by a control system, a sequence of symbols;
   translating, by the control system, the received sequence of symbols into a batch of commands parsable by an electronic controller of the electromechanical medical device;
   sending, by the control system, the batch of commands from the control system to the electromechanical medical device; and
   controlling, by the electronic controller, the electromechanical medical device to perform an electromechanical medical operation by causing the electromechanical medical device to execute the batch of commands on the electromechanical medical device, the electromechanical medical device performing the electromechanical medical operation on a medical patient,
   wherein the translating of the received sequence of symbols is executed using one dictionary among a set of dictionaries, wherein each of the dictionaries in the set of dictionaries has a respective batch of commands parsable by the electronic controller of the electromechanical medical device and respective first sets of symbols corresponding to the respective batch of commands parsable by the electronic controller of the electromechanical medical device for controlling the electromechanical medical device, and
   wherein the translating of the received sequence of symbols includes,
   identifying the set of dictionaries, wherein each first set of symbols of any dictionary of the set of dictionaries comprises a respective symbol being comprised in the received sequence of symbols,
   identifying for each of the dictionaries of the set of dictionaries a respective fragment of the received sequence of symbols comprising one symbol of each of the first sets of symbols of the each of the dictionaries, starting with the symbol comprised in one of the first sets of symbols of the each of the dictionaries, and ending with the symbol comprised in another one of the first sets of symbols of the each of the dictionaries,
   selecting the identified fragment of the received sequence of symbols having the least number of symbols among the identified fragments of the received sequence of symbols, and
   selecting the one dictionary among the set of dictionaries corresponding to the selected identified fragment of the received sequence of symbols,
   wherein the batch of commands of the selected dictionary is the one generated in the translating of the received sequence of symbols into the batch of commands parsable by the electronic controller of the electromechanical medical device, and
   wherein the electromechanical medical device is one of a syringe, a perfusion tool, a magnetic resonance imaging scanner, or an X-Ray tool.

2. The control method of claim 1, wherein the identifying for each of the dictionaries of the set of dictionaries of the respective fragment of the received sequence of symbols comprising one symbol of each of the first sets of symbols of the each of the dictionaries, starting with the symbol comprised in one of the first sets of symbols of the each of the dictionaries, and ending with the symbol comprised in another one of the first sets of symbols the each of the dictionaries; selecting the identified fragment of the received sequence of symbols having the least number of symbols among the identified fragments of the received sequence of symbols; the selecting of the identified fragment of the received sequence of symbols having the least number of symbols among the identified fragments of the received sequence of symbols; and the selecting of the dictionary corresponding to the selected identified fragment of the received sequence of symbols is executed when the set of dictionaries comprises more than one of the dictionaries,
   wherein the translating of the received sequence of symbols into the batch of commands parsable by the electronic controller of the electromechanical medical device comprises:
   selecting the dictionary corresponding to the dictionary comprised in the set of dictionaries when the set of dictionaries consists of one of the dictionaries.

3. The control method of claim 1, wherein
   the translating of the received sequence of symbols into the batch of commands parsable by the electronic controller of the electromechanical medical device comprises generating an error of the translating of the received sequence of symbols into the batch of commands parsable by the electronic controller of the electromechanical medical device, when the set of dictionaries is an empty set or when two or more of the identified fragments of the received sequence of symbols have the same number of symbols being less than a number of symbols in any other, if any, identified fragment of the received sequence of symbols, and the method comprises in response to the generating of the error aborting the translating of the received sequence of symbols into the batch of commands parsable by the electronic controller of the electromechanical medical device.

4. The control method of claim 1, wherein one of the first sets of symbols consists of symbols having synonym meaning.

5. The control method of claim 1, wherein each of the symbols of one of the first sets of symbols is a respective word of a natural language or a respective word combination of the natural language and all symbols of the one of the first sets of symbols are synonyms.

6. The control method of claim 1, wherein each of the dictionaries has a respective order specification determining placing of symbols of its first sets of symbols in sequences of symbols, wherein for any of the dictionaries comprised in the set of dictionaries the symbols each comprised in the respective first set of symbols and in the received sequence of symbols are placed in the received sequence of symbols according to the respective order specification.

7. The control method of claim 6, wherein each of the order specifications complies with a syntax of a natural language.

8. The control method of claim 1, wherein each of the dictionaries comprises a respective maximum allowable number of symbols which can be placed between any of symbols of one of its first sets of symbols and any of symbols of another one of its first sets of symbols in sequences of symbols, wherein for any of the dictionaries comprised in the set of dictionaries a respective number of symbols placed in the received sequence of symbols between two symbols between which the maximum allowable number of symbols is specified, is less or equal to the respective maximum allowable number of symbols.

9. The control method of claim 1, wherein the received sequence of symbols is received from a user electronic interface device, wherein each of the batches of commands parsable by the electronic controller of the electromechanical medical device has a respective description, wherein the method comprises:
  sending the description of the batch of commands of the selected dictionary to the user electronic interface device;
  the user electronic interface device receiving the description of the batch of commands of the selected dictionary;
  the user electronic interface device sending a communication signal to a user for communicating to the user the description of the batch of commands of the selected dictionary;
  the user electronic interface device receiving from the user a communication signal indicating that the description of the batch of commands of the selected dictionary corresponds to the received sequence of symbols;
  the user electronic interface device sending a confirmation message in response to the receiving the communication signal from the user; and
  receiving from the user electronic interface device the confirmation message,
  wherein the sending the batch of commands from the control system to the electromechanical medical device and the causing by the electronic controller of the electromechanical medical device to execute the batch of commands on the electromechanical interface device.

10. The control method of claim 1, wherein each of the batches of commands parsable by the electronic controller of the electromechanical medical device comprises one or more respective parameter fields, wherein each of the parameter fields is associated with respective second sets of symbols and a respective conversion rule for converting symbols into a respective format compatible with the each of the parameter fields, wherein each of some of the parameter fields is associated with a respective default parameter, wherein the translating of the received sequence of symbols into the batch of commands parsable by the electronic controller of the electromechanical medical device comprises, for each of the parameter fields of the batch of commands of the selected dictionary:
  if each criterion of a criteria set is compiled with,
    converting one or more symbols into the respective format using the conversion rule associated with the each of the parameter fields of the batch of commands of the selected dictionary, wherein each of the one or more symbols is comprised in the received sequence of symbols and in the respective second set of symbols associated with the each of the parameter fields of the batch of commands of the selected dictionary; and
    entering the one or more converted symbols in the each of the parameter fields of the batch of commands of the selected dictionary; and
  if at least one criterion of the criteria set is not complied with,
    entering the respective default parameter associated with the each of the parameter fields of the batch of commands of the selected dictionary in the each of the parameter fields of the batch of commands of the selected dictionary when the each of the parameter fields of the batch of commands of the selected dictionary parameter field is associated with the respective default parameter, otherwise generating an error,
  wherein the criteria set comprises the following criterion: each second set of symbols associated with the each of the parameter fields of the batch of commands of the selected dictionary comprises a respective symbol being comprised in the received sequence of symbols.

11. The control method of claim 10, the method comprising:
  in response to the generating of the error aborting the translating of the received sequence of symbols into the batch of commands parsable by the electronic controller of the electromechanical medical device.

12. The control method of claim 10, wherein each of the parameter fields is associated with a respective order specification determining placing of symbols of the second sets associated with it in sequences of symbols, wherein the criteria set comprises the following criterion: the symbols each comprised in the respective second set of symbols associated with the each of the parameter fields of the batch of commands of the selected dictionary and in the received sequence of symbols are placed in the received sequence of symbols according to the order specification associated with the each of the parameter fields of the batch of commands of the selected dictionary.

13. The control method of claim 12, wherein each of the order specifications complies with a syntax of a natural language.

14. The control method of claim 10, wherein each of the parameter fields is associated with a respective maximum allowable number of symbols which can be placed between any of symbols of one of the second sets of symbols associated with it and any of symbols of another one of second sets associated with it in sequences of symbols, wherein the criteria set comprises the following criterion: a number of symbols placed in the received sequence of symbols between two symbols between which the maximum allowable number of symbols is specified, is less or equal to the maximum allowable number of symbols associated with the each of the parameter fields of the batch of commands of the selected dictionary.

15. The control method of claim 10, wherein the received sequence of symbols is received from a user electronic interface device, wherein each of the batches of commands parsable by the electronic controller of the electromechanical medical device has a respective description, wherein each of the parameter fields has a respective description, wherein the method comprises if either the one or more respective converted symbols or the respective default parameter is entered in each of the parameter fields of the batch of commands of the selected dictionary:
  generating a message comprising the description of the batch of commands of the selected dictionary, the description of each of the parameter fields of the batch of commands of the selected dictionary and either the one or more respective converted symbols or the respective default parameter being entered therein;
  sending the message to the user electronic interface device;
  the user electronic interface device sending to a communication signal to a user for communicating to the user the message;
  the user electronic interface device receiving from the user a communication signal indicating that the description of the batch of commands of the selected dictionary corresponds to the received sequence of symbols and the parameter fields of the batch of commands of the selected dictionary are filled in correctly;
  the user electronic interface device sending a confirmation message in response to the receiving the signal from the user; and
  receiving from the user electronic interface device the confirmation message,
  wherein the sending the batch of commands from the control system to the electromechanical medical device and the causing by the electronic controller of the electromechanical medical device to execute the batch of commands on the electromechanical medical device is executed when the confirmation message is received from the user electronic interface device.

16. The control method of claim 10, the method comprising, before execution of the operations which are executed for the each of the parameter fields of the batch of commands of the selected dictionary:
  generating an auxiliary set of symbols, wherein a number of symbols in the auxiliary set is equal to a number of the first sets in the selected dictionary, wherein each of the symbols comprised in the auxiliary set is comprised in one of the first dictionaries of the selected dictionary and in the received sequence of symbols; and
  deleting each symbol of the auxiliary set from the received sequence of symbols.

17. The control method of claim 1, wherein the received sequence of symbols is a phrase in a natural language.

18. A non-transitory computer readable medium having stored thereon a computer executable code for execution by a computer processor controlling a control system, wherein execution of instructions of the executable code causes the computer processor to execute the control method of claim 1.

19. A control system for controlling an electromechanical medical device, wherein the control system comprises a computer processor and a memory storing instructions of a computer executable code which execution by the computer processor causes the control system to perform the following:
  receiving, by the control system, a sequence of symbols;
  translating the received sequence of symbols into a batch of commands parsable by an electronic controller of the electromechanical medical device;
  sending the batch of commands from the control system to the electromechanical medical device; and
  controlling, by the electronic controller, the electromechanical medical device to perform an electromechanical medical operation by causing the electromechanical medical device to execute the batch of commands on the electromechanical medical device, the electromechanical medical device performing the electromechanical medical operation on a medical patient,
  wherein the translating of the received sequence of symbols is executed using one dictionary among a set of dictionaries, wherein each of the dictionaries in the set of dictionaries has a respective batch of commands parsable by the electronic controller of the electromechanical medical device and respective first sets of symbols corresponding to the respective batch of commands parsable by the electronic controller of the electromechanical medical device for controlling the electromechanical medical device, and
  wherein the translating of the received sequence of symbols includes,
    identifying the set of dictionaries, wherein each first set of symbols of any dictionary of the set of dictionaries comprises a respective symbol being comprised in the received sequence of symbols,
    identifying for each of the dictionaries of the set of dictionaries a respective fragment of the received sequence of symbols comprising one symbol of each of the first sets of symbols of the each of the dictionaries, starting with the symbol comprised in one of the first sets of symbols of the each of the dictionaries, and ending with the symbol comprised in another one of the first sets of symbols of the each of the dictionaries,
    selecting the identified fragment of the received sequence of symbols having the least number of symbols among the identified fragments of the received sequence of symbols, and
    selecting the one dictionary among the set of dictionaries corresponding to the selected identified fragment of the received sequence of symbols, and
  wherein the batch of commands of the selected dictionary is the one generated in the translating of the received sequence of symbols into the batch of commands parsable by the electronic controller of the electromechanical medical device, and
  wherein the electromechanical medical device is one of a syringe, a perfusion tool, a magnetic resonance imaging scanner, or an X-Ray tool.

* * * * *